US006239155B1

(12) United States Patent
Meier et al.

(10) Patent No.: US 6,239,155 B1
(45) Date of Patent: *May 29, 2001

(54) PHENYL-SUBSTITUTED 1,4-DIHYDROPYRIDINES

(75) Inventors: Heinrich Meier, Kobe (JP); Wolfgang Hartwig, Stamford, CT (US); Bodo Junge; Rudolf Schohe-Loop, both of Wuppertal (DE); Zhan Gao, Beijing (CN); Bernard Schmidt, Lindlar (DE); Maarten de Jonge, Overath (DE); Teunis Schuurman, Lohmar (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/348,399

(22) Filed: Dec. 2, 1994

(30) Foreign Application Priority Data

Dec. 10, 1993 (DE) ................................. 43 42 194
Dec. 10, 1993 (DE) ................................. 43 42 196

(51) Int. Cl.⁷ ........................ C07D 211/86; A61K 31/455
(52) U.S. Cl. ............................................ 514/356; 546/321
(58) Field of Search .......................... 546/321; 514/356

(56) References Cited

U.S. PATENT DOCUMENTS

| | | | |
|---|---|---|---|
| 3,764,683 | * 10/1973 | Bossert et al. | 514/356 |
| 3,932,646 | 1/1976 | Meyer et al. | 546/321 |
| 3,966,946 | 6/1976 | Roe et al. | 546/321 |
| 4,264,611 | * 4/1981 | Berntsson et al. | 546/321 |
| 4,406,906 | 9/1983 | Meyer et al. | 514/321 |
| 4,497,821 | * 2/1985 | Wehinger et al. | 514/302 |
| 4,510,310 | 4/1985 | Wehinger et al. | 546/321 |
| 4,559,350 | 12/1985 | Wehinger et al. | 514/332 |
| 4,568,681 | 2/1986 | Wehinger et al. | 546/321 |
| 4,622,332 | 11/1986 | Wehinger et al. | 546/321 |
| 4,786,641 | * 11/1988 | Goldmann et al. | 514/302 |
| 4,849,433 | 7/1989 | Wehinger et al. | 546/321 |
| 4,918,076 | 4/1990 | Opitz et al. | 514/277 |
| 4,956,361 | 9/1990 | Traber et al. | 514/356 |
| 4,988,717 | 1/1991 | Wehinger et al. | 546/321 |
| 5,114,946 | 5/1992 | Lawter et al. | 514/279 |
| 5,137,889 | 8/1992 | Tamada et al. | 514/252 |
| 5,234,935 | * 8/1993 | Behner et al. | 546/321 |
| 5,310,917 | * 5/1994 | Auerbach | 546/249 |
| 5,328,931 | * 7/1994 | Rosen et al. | 546/356 |
| 5,403,849 | * 4/1995 | Schohe-Loop et al. | 546/281 |

FOREIGN PATENT DOCUMENTS

| | | |
|---|---|---|
| 151485 | 10/1970 | (AU) . |
| 0007293 | 1/1980 | (EP) . |
| 0088940 | 9/1983 | (EP) . |
| 0525568 | 2/1993 | (EP) . |
| 0534520 | 3/1993 | (EP) . |
| 0595164 | 5/1994 | (EP) . |

OTHER PUBLICATIONS

Appel, Current Neurology, vol. 6 p. 289, 315, 1987.*
Clark et al. Principles of Psychopharmacology, p. 166–167, 1970.*
Ca 103 : 123371. 1985.*
Aldrichimica Acta, vol. 18, p. 25 (1985).
Still et al. J. Org. Chem. vol.43, No. 14, 2923, (1978).
Rampe D.R., Mutledge A., Janis R.A., Triggle D.J.: Can. Journ. Physiol. Pharacol. vol. 65, 1452, (1987).
Journel of Cardiovascular Pharmacology, vol. 10 (1987) pp. S60–S65.

* cited by examiner

Primary Examiner—Jane Fan
(74) Attorney, Agent, or Firm—Norris McLaughlin & Marcus

(57) ABSTRACT

Novel phenyl-substituted 1,4-dihydropyridines, prepared by reacting halogenophenyl-aldehydes with β-ketoesters, if appropriate with isolation of the ylidene compounds and enamines. The substances can be employed as active compounds in medicaments, in particular in cerebrally active compositions.

4 Claims, No Drawings

PHENYL-SUBSTITUTED 1,4-DIHYDROPYRIDINES

The invention relates to novel phenyl-substituted 1,4-dihydropyridines, processes for their preparation and their use in medicaments, in particular as cerebrally active agents.

It has been disclosed that some dihydropyridines, such as e.g. nimodipine, have cerebral activity [cf. German Offenlegungsschrift 28 15 578]. Dihydropyridines having circulatory activity have also been disclosed which in the 4-position carry a phenyl ring which is substituted by halogen, CN or $CF_3$ [cf. German Offenlegungsschrift 1 963 188, German Offenlegungsschrift 2 117 572, German Offenlegungsschrift 2 117 573 and BP 007 293).

The present invention relates to selected new 4-phenyl-substituted 1,4-dihydropyridines of the general formula (I)

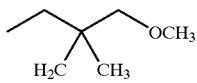

in which
$R^1$ and $R^3$ are identical or different and represent straight-chain or branched alkyl having up to 8 carbon atoms, which is optionally substituted by straight-chain or branched alkoxy having up to 6 carbon atoms or hydroxyl, or represent cycloalkyl having 3 to 7 carbon atoms,
and $R^2$ represents the radical

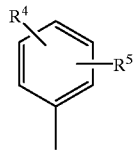

in which
$R^4$ and $R^5$ are identical or different and represent halogen, cyano, ethinyl, trifluoromethoxy, methyl, methylthio, trifluoromethyl or straight-chain or branched alkoxy having up to 4 carbon atoms,
or
$R^4$ or $R^5$ represents hydrogen
and their salts, in particular the new compounds of exemplary embodiments 1–124 coming under the formula (I).

Physiologically acceptable salts are salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention exist in stereoisomeric forms which either behave as image and mirror image (enantiomers), or which do not behave as image and mirror image (diastereomers). The invention relates both to the antipodes and to the racemic forms as well as the diastereomer mixtures. Like the diastereomers, the racemic forms can also be separated in a known manner into the stereoisomerically uniform constituents.

Preferred compounds are those of the general formula (I) in which
$R^1$ and $R^3$ are identical or different and represent straight-chain or branched alkyl having up to 8 carbon atoms, which is optionally substituted by straight-chain or branched alkoxy having up to 5 carbon atoms or hydroxyl, or represent cyclopropyl, cyclopentyl, cyclohexyl or cycloheptyl,
and $R^2$ represents the radical

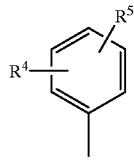

in which
$R^4$ and $R^5$ are identical or different and represent fluorine, bromine, chlorine, cyano, ethinyl, trifluoromethoxy, methyl, methylthio, trifluoromethyl or straight-chain or branched alkoxy having up to 3 carbon atoms, or
$R^4$ or $R^5$ represents hydrogen
and their salts.

Particularly to be emphasized are new compounds of the general formula I, in which $R^3$ represents the radical $-(CH_2)_n-OR^6$, in which n represents a number from 2 to 4 and $R^6$ represents hydrogen or alkyl having 1 to 4 C atoms, in particular compounds of the formula I in which $R^3$ represents the radical $-CH_2-CH_2-OCH_3$, and $R^1$ is identical to or different from $R^3$ and represents straight-chain or branched alkyl having up to 8 carbon atoms, which is optionally substituted by hydroxyl or alkoxy having 1 to 4 C atoms, or represents cyclopropyl, cyclopentyl, cyclohexyl or cycloheptyl.

Of particular interest are compounds of the general formula I in which $R^2$ represents a cyanophenyl radical which as a second phenyl substituent carries fluorine, chlorine or $CF_3$. Of particular interest are also those compounds of the general formula I which in the 2- and 3-position of the phenyl radical $R^2$ are substituted by substituents from the group consisting of chlorine, fluorine, cyano and $CF_3$, the 2,3-dichlorophenyl radical being excluded.

Very particularly preferred compounds of the general formula (I) are the following:
(±) isopropyl 2-methoxyethyl 4-(2-fluorophenyl)-1,4-dihydro-2,6-dimethylpyridine-3,5-dicarboxylate
(+) isopropyl 2-methoxyethyl 4-(2-fluorophenyl)-1,4-dihydro-2,6-dimethylpyridine-3,5-dicarboxylate
(−) isopropyl 2-methoxyethyl 4-(2-fluorophenyl)-1,4-dihydro-2,6-dimethylpyridine-3,5-dicarboxylate
(±) isopropyl 2-methoxyethyl 4-(2,3-difluorophenyl)-1,4-dihydro-2,6-dimethylpyridine-3,5-dicarboxylate
(+) isopropyl 2-methoxyethyl 4-(2,3-difluorophenyl)-1,4-dihydro-2,6-dimethylpyridine-3,5-dicarboxylate
(−) isopropyl 2-methoxyethyl 4-(2,3-difluorophenyl)-1,4-dihydro-2,6-dimethylpyridine-3,5-dicarboxylate
(±) isopropyl 2-methoxyethyl 4-(2,5-difluorophenyl)-1,4-dihydro-2,6-dimethylpyridine-3,5-dicarboxylate
(+) isopropyl 2-methoxyethyl 4-(2,5-difluorophenyl)-1,4-dihydro-2,6-dimethylpyridine-3,5-dicarboxylate
(−) isopropyl 2-methoxyethyl 4-(2,5-difluorophenyl)-1,4-dihydro-2,6-dimethylpyridine-3,5-dicarboxylate
(±) isopropyl 2-methoxyethyl 4-(2,6-difluorophenyl)-1,4-dihydro-2,6-dimethylpyridine-3,5-dicarboxylate
(+) isopropyl 2-methoxyethyl 4-(2,6-difluorophenyl)-1,4-dihydro-2,6-dimethylpyridine-3,5-dicarboxylate (−) isopropyl 2-methoxyethyl 4-(2,6-difluorophenyl)-1,4-dihydro-2,6-dimethylpyridine-3,5-dicarboxylate (±) isopropyl 2-methoxyethyl 4-(2,5-dichlorophenyl)-1,4-dihydro-2,6-dimethylpyridine-3,5-dicarboxylate (+) isopropyl 2-methoxyethyl 4-(2,5-dichlorophenyl)-1,4-dihydro-2,6-dimethylpyridine-3,5-dicarboxylate (−) isopropyl 2-methoxyethyl 4-(2,5-dichlorophenyl)-1,4-dihydro-2,6-dimethylpyridine-3,5-dicarboxylate (±) isopropyl 2-methoxyethyl 4-(2-chloro-6-fluorophenyl)-1,4-dihydro-2,6-dimethylpyridine-3,5-dicarboxylate (+) isopropyl 2-methoxyethyl 4-(2-chloro-6-fluorophenyl)-1,4-dihydro-2,6-dimethylpyridine-3,5-dicarboxylate (−) isopropyl 2-methoxyethyl 4-(2-chloro-6-fluorophenyl)-1,4-dihydro-2,6-dimethylpyridine-3,5-dicarboxylate (±) isopropyl 2-methoxyethyl 4-(2-fluoro-3-trifluoromethylphenyl)-1,4-dihydro-2,6-dimethyl-pyridine-3,5-dicarboxylate (+) isopropyl 2-methoxyethyl 4-(2-fluoro-3-trifluoromethylphenyl)-1,4-dihydro-2,6-dimethyl-pyridine-3,5-dicarboxylate (−) isopropyl 2-methoxyethyl 4-(2-fluoro-3-trifluoromethylphenyl)-1,4-dihydro-2,6-dimethyl-pyridine-3,5-dicarboxylate (±) isopropyl 2-methoxyethyl 4-(3-chloro-2-cyanophenyl)-1,4-dihydro-2,6-dimethylpyridine-3,5-dicarboxylate (+) isopropyl 2-methoxyethyl 4-(3-chloro-2-cyanophenyl)-1,4-dihydro-2,6-dimethylpyridine-3,5-dicarboxylate (−) isopropyl 2-methoxyethyl 4-(3-chloro-2-cyanophenyl)-1,4-dihydro-2,6-dimethylpyridine-3,5-dicarboxylate (±) isopropyl 2-methoxyethyl 4-(2-cyanophenyl),-1,4-dihydro-2,6-dimethylpyridine-3,5-dicarboxylate (+) isopropyl 2-methoxyethyl 4-(2-cyanophenyl)-1,4-dihydro-2,6-dimethylpyridine-3,5-dicarboxylate (−) isopropyl 2-methoxyethyl 4-(2-cyanophenyl)-1,4-dihydro-2,6-dimethylpyridine-3,5-dicarboxylate (±) tert-butyl 2-methoxyethyl 4-(3-cyanophenyl)-1,4-dihydro-2,6-dimethylpyridine-3,5-dicarboxylate (+) tert-butyl 2-methoxyethyl 4-(3-cyanophenyl)-1,4-dihydro-2,6-dimethylpyridine-3,5-dicarboxylate (−) tert-butyl 2-methoxyethyl 4-(3-cyanophenyl)-1,4-dihydro-2,6-dimethylpyridine-3,5-dicarboxylate (±) cycloheptyl 2-methoxyethyl-4-(3-cyanophenyl)-1,4-dihydro-2,6-dimethylpyridine-3,5-dicarboxylate (+) cycloheptyl 2-methoxyethyl 4-(3-cyanophenyl)-1,4-dihydro-2,6-dimethylpyridine-3,5-dicarboxylate (−) cycloheptyl 2-methoxyethyl 4-(3-cyanophenyl)-1,4-dihydro-2,6-dimethylpyridine-3,5-dicarboxylate (±) cyclopentyl 2-methoxyethyl 4-(2-chloro-3-cyanophenyl)-1,4-dihydro-2,6-dimethylpyridine-3,5-dicarboxylate (+) cyclopentyl 2-methoxyethyl 4-(2-chloro-3-cyanophenyl)-1,4-dihydro-2,6-dimethylpyridine-3,5-dicarboxylate (−) cyclopentyl 2-methoxyethyl 4-(2-chloro-3-cyanophenyl)-1,4-dihydro-2,6-dimethylpyridine-3,5-dicarboxylate (±) cyclopentyl 2-methoxyethyl 4-(2-fluoro-3-trifluoromethylphenyl)-1,4-dihydro-2,6-dimethyl-pyridine-3,5-dicarboxylate (+) cyclopentyl 2-methoxyethyl 4-(2-fluoro-3-trifluoromethylphenyl)-1,4-dihydro-2,6-dimethyl-pyridine-3,5-dicarboxylate (−) cyclopentyl 2-methoxyethyl 4-(2-fluoro-3-trifluoromethylphenyl)-1,4-dihydro-2,6-dimethyl-pyridine-3,5-dicarboxylate (±) 2-methoxyethyl methyl 4-(2-fluoro-3-trifluoromethylphenyl)-1,4-dihydro-2,6-dimethyl-pyridine-3,5-dicarboxylate (+) 2-methoxyethyl methyl 4-(2-fluoro-3-trifluoromethylphenyl)-1,4-dihydro-2,6-dimethyl-pyridine-3,5-dicarboxylate (−) 2-methoxyethyl methyl 4-(2-fluoro-3-trifluoromethylphenyl)-1,4-dihydro-2,6-dimethyl-pyridine-3,5-dicarboxylate (±) cyclopentyl 2-methoxyethyl 4-(2-cyano-3-chlorophenyl)-1,4-dihydro-2,6-dimethylpyridine-3,5-dicarboxylate (+) cyclopentyl 2-methoxyethyl 4-(2-cyano-3-chlorophenyl)-1,4-dihydro-2,6-dimethylpyridine-3,5-dicarboxylate (−) cyclopentyl 2-methoxyethyl 4-(2-cyano-3-chlorophenyl)-1,4-dihydro-2,6-dimethylpyridine-3,5-dicarboxylate.

The invention also relates to processes for the preparation of the compounds of the general formula (I) according to the invention, characterized in that

[A] aldehydes of the general formula (II)

$$R^2\text{—CHO} \qquad (II)$$

in which $R^2$ has the meaning indicated, are reacted first with acetoacetic esters of the general formula (III)

$$H_3C\text{—CO—CH}_2\text{—CO}_2R^1 \qquad (III)$$

in which $R^1$ has the meaning indicated, if appropriate with isolation of the corresponding ylidene compounds of the general formula (IV)

(IV)

in which $R^1$ and $R^2$ have the meaning indicated, and these are then reacted either with compounds of the general formula (V)

$$CH_3\text{—CO—CH}_2\text{—CO}_2R^3 \qquad (V)$$

in which $R^3$ has the meaning indicated, in inert solvents, in the presence of ammonia or ammonium salts, or directly with enamino derivatives of the general formula (VI)

(VI)

in which $R^3$ has the meaning indicated, or

[B] the aldehydes of the general formula (II) are reacted first with the compounds of the general formula (V), if appropriate with isolation of the ylidene compounds of the general formula (VII)

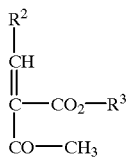
(VII)

in which

R² and R³ have the meaning indicated, and these are reacted in a next step with the compounds of the general formula (III) in inert solvents, in the presence of ammonia or ammonium salts or directly with enaminocarboxylic acid derivatives of the general formula (VIII)

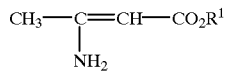
(VIII)

in which

R¹ has the meaning indicated, or

[C] compounds of the general formula (IX)

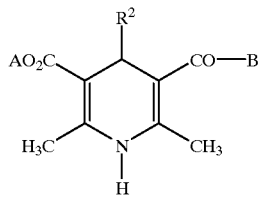
(IX)

in which

R² has the meaning indicated above,

A has the meaning of R¹ or R³ indicated above and

B together with the —CO— group forms a reactive carboxylic acid derivative, are reacted in inert solvents, in the presence of a base, with compounds of the general formula (X)

 —OH   (X)

in which

R⁶ has the meaning of R¹ or R³ indicated, and in the case of the pure ester enantiomers, the enantiomerically pure carboxylic acids are reacted, if appropriate first via the stage of a reactive acid derivative, with the corresponding alcohols.

The process according to the invention can be illustrated by way of example by the following reaction scheme:

[A]

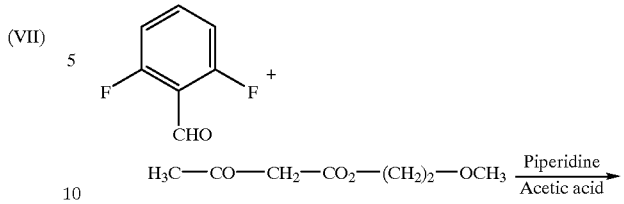

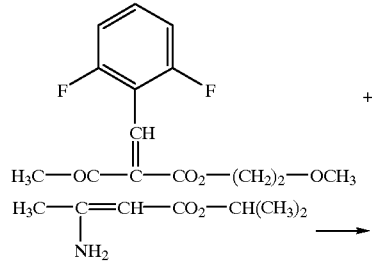

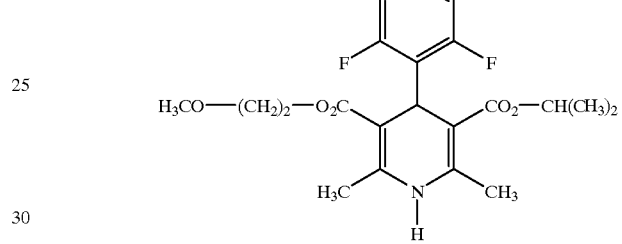

[B]

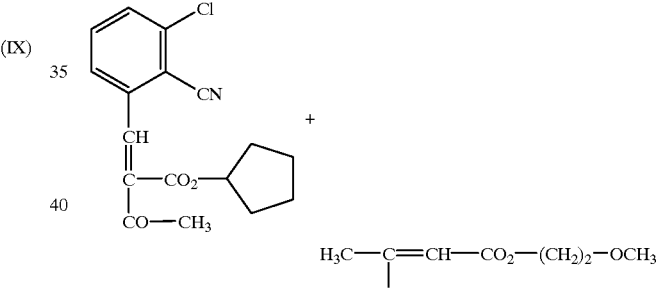

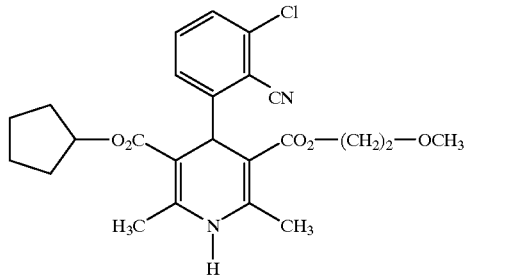

[C]

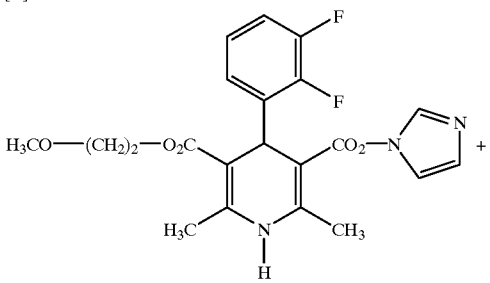

-continued

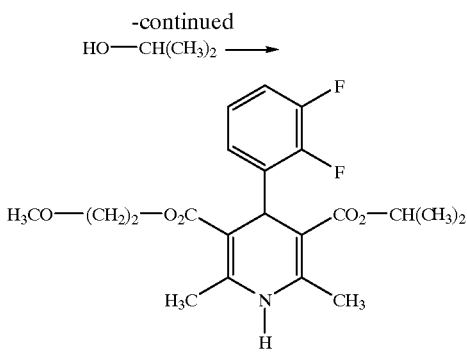

Suitable solvents for processes [A] and [B] in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene or toluene. It is also possible to use mixtures of the solvents mentioned. Isopropanol, tetrahydrofuran, methanol, dioxane and dimethylformamide are preferred.

Suitable solvents for process [C] are the abovementioned solvents with the exception of the alcohols and acetic acid.

Suitable bases are in general cyclic amines, such as, for example, piperidine, $C_1$–$C_3$-tri- and dialkylamines, such as, for example, di- and triethylamine or pyridine or dimethylaminopyridine. Depending on the particular reaction steps, piperidine, dimethylaminopyridine and pyridine are preferred.

The auxiliaries employed are preferably condensing agents which can also be bases. The customary condensing agents are preferred here such as carbodiimides e.g. N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphonate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)phosphonium hexafluorophosphonate. N,N'-Dicyclohexylcarbodiimide and carbonyldiimidazole are preferred.

Suitable bases for the activation of the carboxylic acids are in general alkali metal carbonates such as, for example, sodium carbonate or potassium carbonate, or organic bases such as trialkylamines, e.g. triethylamine, N-ethylmorpholine, N-methylpiperidine or diisopropylethylamine, or dimethylaminopyridine, 1,8-diazabicyclo-[5.4.0]undec-7-ene (DBU) or 1,5-diazabicyclo [4.3.0]non-5-ene (DBN). Dimethylaminopyridine is preferred.

The base is in general employed in an amount from 0.01 mol to 1 mol, preferably from 0.05 mol to 0.1 mol, in each case relative to 1 mol of the compounds of the general formulae (II) and (IX).

The auxiliaries are in general employed in an amount from 1 mol to 3 mol, preferably from 1 mol to 1.5 mol, in each case relative to 1 mol of the compounds of the general formulae (II) and (IX).

The reaction temperatures for processes [A] and [B] can be varied within a relatively wide range. In general, the reaction is carried out in a range from –20° C. to 200° C., preferably from 0° C. to 110° C.

The processes can be carried out at normal pressure, elevated pressure or reduced pressure (for example from 0.5 to 5 bar), preferably at normal pressure.

When carrying out the processes according to the invention, any desired ratio of the substances participating in the reaction can be used. In general, however, the reaction is carried out with molar amounts of the reactants.

Reagents suitable for the activation of the carboxylic acid are the customary reagents such as inorganic halides, for example thionyl chloride, phosphorus trichloride or phosphorus pentachloride, or carbonyldiimidazole, carbodiimides such as cyclohexylcarbodimide or 1-cyclohexyl-3-[2-(N-methylmorpholino)ethyl]-carbodiimide p-toluenesulphonate or N-hydroxyphthalimide or N-hydroxy-benzotriazole.

Enantiomerically pure forms are obtained e.g. additionally by separating diastereomer mixtures of the compounds of the general formula (I) in which $R^1$ or $R^3$ represents an enantiomerically pure chiral alcohol radical, according to a customary method, subsequently preparing the enantiomerically pure carboxylic acids and then optionally converting into the enantiomerically pure dihydropyridines by esterification with appropriate alcohols.

Suitable chiral ester radicals are all esters of enantiomerically pure alcohols such as, for example, 1-phenylethanol, lactic acid, lactic acid esters, mandelic acid, mandelic acid esters, 2-aminoalcohols, sugar derivatives and many other enantiomerically pure alcohols.

The separation of the diastereomers is in general carried out either by fractional crystallization, by column chromatography or by countercurrent distribution. Which is the optimum process must be decided from case to case; sometimes it is also expedient to utilize combinations of the individual processes.

The esterification of the enantiomerically pure dihydropyridines is preferably carried out in ethers such as diethyl ether or tetrahydrofuran, in dimethylformamide, methylene chloride, chloroform, acetonitrile or toluene.

The aldehydes of the general formula (II) are known per se or can be prepared by customary methods.

The acetoacetic esters of the general formulae (III) and (V) and the enamino derivatives of the general formulae (VI) and (VIII) are also known.

The reactive acid derivatives of the general formula (IX) are known in some cases or are new and can then be prepared by customary methods.

The compounds of the general formula (X) are known.

The compounds of the general formulae (IV) and (VII) are mostly known or can be prepared by customary methods.

The above preparation processes are only given for clarification. The preparation of the compounds of the general formula (I) is not restricted to these processes, but any modification of these processes is applicable in the same manner for the preparation of the compounds according to the invention.

The compounds according to the invention show an unforeseeable, useful spectrum of pharmacological activity.

The compounds according to the invention are calcium channel ligands with selectivity for L-type calcium channels of the central nervous system. This selectivity can be seen, for example, by comparison of the binding affinities to DEP binding sites in rats' brains and rats' hearts.

The compounds positively affect learning and memory performance, as their performance-enhancing effect on rats in typical learning and memory models such as the water maze, Morris maze, passive avoidance and memory tests in automated Skinner boxes demonstrates. They have an antidepressant potential, as their activity in the rat swimming tests according to Porsolt confirms.

Calcium Flux

To determine the calcium flux, a suspension of cultured PC 12 cells is used. The cells are incubated at 37° C. in a customary culture medium together with the active compound to be investigated. To depolarize the cells, an activation medium having a high potassium concentration is added which at the same time contains radioactive calcium ($^{45}Ca^{2+}$). After a specific time interval, a medium cooled to 0° C. is added in order to stop the influx of radioactive calcium into the cells. The radioactivity in the harvested and dried cells is then determined. To determine the 0% limit of the inhibitory value, dimethyl sulphoxide (DMSO) is employed and the 100% inhibitory value is determined using $10^{-6}$ mol/l pimozide.

Binding Assays

The binding affinities to PN 200-110 binding sites in rats' brains or rats' hearts are determined according to Rampe, D. R., Rutledge, A., Janis, R. A., Triggle, D. J.: Can. Journ. Physiol. Pharmacol. 65, (1987) 1452.

Water Maze

Old Wistar rats (24 months) are placed in the starting position in a plastic tank (120×50×40 cm) filled with cold (14–15°) water and subdivided by vertical barriers. In order to reach a ladder which enables the animals to escape from the water, they must swim around these barriers. The time which is required for finding the exit and the number of errors on the way there are recorded. In this case, an error is defined as swimming up a blind alley or swimming over the boundary of imaginary squares into which the tank is subdivided in the direction away from the exit.

The rats remain in the maze until finding the exit, but at longest 300 sec. They are then taken out, dried and warmed under a red light. They then return to their home cages.

In a typical experiment, two equivalent animal groups (placebo, test substance each n=15) are determined by means of a preliminary test. The animals then go through 6 test sessions, two per day. Test substances or placebo are administered orally 30 min before the experiments. The measures of the learning- and memory-enhancing effect of the test substances in comparison to placebo are reduction of the time until reaching the exit, reduction of the number of errors and increase in the number of animals which find the exit at all.

Rat Swimming Test According to Porsolt

During a preliminary test, young rats are placed in a glass cylinder (40 cm high, 20 cm diameter) which is filled 17 cm high with water at 25° C. After 20 min in the water, the animals are taken out and warmed under a lamp for 30 min. In this preliminary test, all rats attempt to get out of the cylinder until after about 15 min they remain immobile ("behavioural despair", giving-up behaviour). 24 h later, the test session starts in which the rats are placed in the glass cylinder as on the previous day, but this time for only 5 min. The lengths of time for which the rats remain immobile during these 5 min are recorded. In this case, a rat is regarded as immobile which, floating upright in the water, only carries out minimal movements in order to keep its head above water. Placebo or test substances (0.25, 0.5, 1, 5, 10 mg/kg; n=6 per group) are administered orally three times; 23, 5 and 1 h before the test session (1, 19, 23 h after the preliminary test). The antidepressant effect of the test substances is seen in the reduction of the period of immobility in comparison to the placebo values.

As a result of their pharmacological properties, the compounds according to the invention can be employed for the preparation of medicaments for the treatment of central degenerative disorders, as, for example, occur in dementias (multi-infarct dementia, MID, primary degenerative dementia PDD, pre- and senile Alzheimer's disease, HIV dementia and other forms of dementia), Parkinson's disease or amyotrophic lateral sclerosis.

The active compounds are furthermore suitable for the treatment of cerebral function disorders in old age, of organic brain syndrome (OBS) and of age-associated memory impairment (AAMI).

They are useful for the prophylaxis and for the control of the sequelae of cerebral circulatory disorders such as cerebral ischaemias, strokes and of subarachnoid haemorrhages and for the treatment of brain traumas.

They are suitable for the treatment of depressions and of mania. Further areas of application are the treatment of migraine, of neuropathies which are caused e.g. by traumas, metabolic disorders such as diabetes mellitus, intoxications, microogranisms or autoimmune disorders, of addictive disorders and withdrawal symptoms.

The compounds according to the invention are $Ca^{2+}$ antagonists with selectivity for L-type $Ca^{2+}$ channels of the central nervous system.

This selectivity exceeds that of the known cerebrally active $Ca^{2+}$-antagonistic dihydropyridines nimodipine and nicardipine. This is seen e.g. in the comparison of the binding affinities to DHP (PN-200 110) binding sites in rats' brain and rats' heart [cf. Rampe, D. R., Rutledge, A., Janis, R. A., Triggle, D. J., Can. Journ. Physiol. Pharmacol. 65 (1987), 1452].

| Ex. No. | $K_i$ (Brain) [nM] | $K_i$ (Heart) [nM] | Selectivity |
|---|---|---|---|
| Nimodipine | 2.4 | 4.6 | 1.9 |
| Nicardipine | 32 | 14 | 0.44 |
| 12 | 7.2 | 72 | 10 |
| 15 | 2.0 | 11.3 | 5.7 |
| 18 | 8.2 | 28 | 3.4 |
| 30 | 1.7 | 8.0 | 4.7 |
| 33 | 3.6 | 7.9 | 2.2 |

The present invention also includes pharmaceutical preparations which, in addition to inert, non-toxic, pharmaceutically suitable auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the excipient(s) or auxiliary(-ies).

In general, it has proven advantageous to administer the active compound(s) of the formula (I) in total amounts of about 0.01 to about 100 mg/kg, preferably in total amounts of about 0.1 mg/kg to 20 mg/kg of body weight every 24 hours, if appropriate in the form of several individual doses, to achieve the desired result.

However, it may sometimes be advantageous to deviate from the amounts mentioned, namely depending on the type and the body weight of the subject treated, on individual behaviour towards the medicament, the nature and severity of the disorder, the type of preparation and administration, and the time and interval at which administration takes place.

The $R_f$ values shown in each case were determined—if not stated otherwise—by thin layer chromatography on silica gel (aluminium foil, silica gel 60 F 254, E. Merck). The substance spots were visualized by observation under UV light and/or by spraying with 1% strength potassium permanganate solution or with molybdophosphoric acid solution.

Flash chromatography was carried out on silica gel 60, 0.040–0.064 mm, E. Merck (see Still et al., J. Org. Chem. 43, 2923, 1978; for simpler separation problems see Aldrichimica Acta 18. 25. 1985). Elution with solvent gradients means: starting with the pure, non-polar solvent mixture component, the polar eluent component is admixed to an increasing extent until the desired product is eluted (TLC checking).

In the case of all products, the solvent was finally distilled off at about 0.1 mm tlg.

STARTING COMPOUNDS

Example I

2-Methoxyethyl 2-acetyl-3-(2-fluorophenyl)-2-propenoate

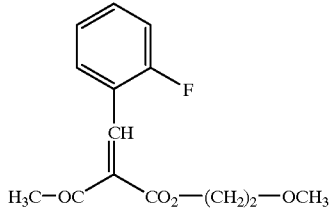

10 g (80 mmol) of 2-fluorobenzaldehyde are dissolved in 200 ml of isopropanol with 13 g (80 mmol) of 2-methoxyethyl acetoacetate. A freshly prepared solution of 1.0 ml of piperidine and 0.5 ml of glacial acetic acid in 10 ml of isopropanol is added to this solution and it is stirred overnight at 40° C. The mixture is concentrated, the residue is taken up in toluene, the solution is concentrated again and the residue is purified by filtration on 300 ml of silica gel (eluent: toluene/ethyl acetate 100:1–10:1) to give 15 g of the target compound as a yellow oil which is immediately reacted further.

Example II

2-Methoxyethyl 2-acetyl-3-(2,4-difluorophenyl)-2-propenoate

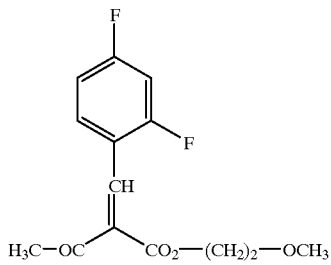

5.0 g (35 mmol) of 2,4-difluorobenzaldehyde are dissolved in 100 ml of isopropanol with 5.7 g (35 mmol) of 2-methoxyethyl acetoacetate. A freshly prepared solution of 1.0 ml of piperidine and 0.5 ml of glacial acetic acid in 5 ml of isopropanol is added to this solution and it is stirred overnight at 40° C. The mixture is concentrated, the residue is taken up in toluene, the solution is concentrated again and the residue is purified by filtration on 100 ml of silica gel (eluent: toluene/ethyl acetate 100:1) to give 5 g of the target compound as a yellow oil which is immediately reacted further.

Example III 4-(2-Chloro-6-fluorophenyl)-3-cyclopentyloxycarbonyl-1,4-dihydro-2,6-dimethylpyridine-5-carboxylic Acid

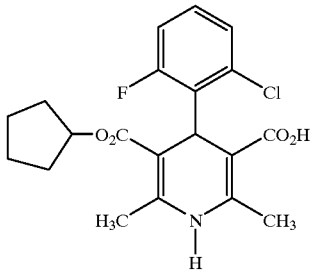

98 g (0.22 mol) of 4-(2-chloro-6-fluorophenyl)-3-(2-cyanoethyl)-cyclopentyloxycarbonyl-1,4-dihydro-2,6-dimethylpyridine-5-carboxylic acid are dissolved in 400 ml of 1,2-dimethoxyethane and the mixture is stirred at room temperature overnight with 400 ml of 1 N sodium hydroxide solution. The solvent volume is reduced to about half, the solution is washed with dichloromethane and the aqueous phase is acidified with 2 N hydrochloric acid (pH=2). Extraction twice with dichloromethane, washing of the organic phase with water, drying over sodium sulphate, concentration and crystallization from ether yields 42 g of the target compound as a solid of melting point about 120° C. (dec.).

Example IV

Cyclopentyl 4-(2-chloro-6-fluorophenyl)-1,4-dihydro-5-(1-imidazolylcarbonyl)-2,6-dimethylpyridine-3-carboxylate

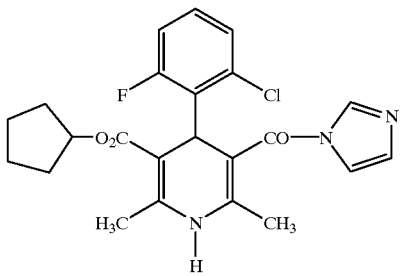

13.6 g (83 mmol) of carbonyldiimidazole are added to 33.0 g (83 mmol) of 4-(2-chloro-6-fluorophenyl)-3-cyclopentyloxycarbonyl-1,4-dihydro-2,6-dimethylpyridine-5-carboxylic acid in 350 ml of tetrahydrofuran and the mixture is heated to reflux for 3 h. Thin-layer chromatographic checking (silica gel, toluene/ethyl acetate 1:1) shows complete reaction, after which the reaction mixture is concentrated, the residue is taken up in ethyl acetate, and the solution is washed twice with water, dried over sodium sulphate and concentrated again. The target compound precipitates from ether in the form of white crystals of m.p. 150° C.

Yield: 29.7 g

PREPARATION EXAMPLES

Example 1

Isopropyl 2-methoxyethyl 4-(2-fluorophenyl)-1,4-dihydro-2,6-dimethylpyridine-3,5-dicarboxylate

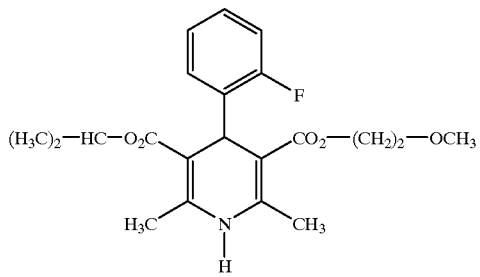

4.0 g (about 15 mmol) of the compound from Example I are heated to reflux overnight in 100 ml of isopropanol with 2.2 g (15 mmol) of isopropyl 3-amino-2-butenoate. After thin-layer chromatographic checking (SiO$_2$, toluene/ethyl acetate 5:1) shows complete conversion, the reaction mixture is concentrated, the residue is-taken up with toluene, the solution is concentrated again and the residue is then purified by filtration on silica gel (eluent: toluene/ethyl acetate 100:1–5:1). A crystallizing yellow oil is obtained, which is recrystallized from methanol at about –15° C. 2.8 g (48%) of the target compound are obtained.

M.p.: 99–100° C.

Example 2
(–)-Cycloheptyl 2-methoxyethyl 4-(3-cyanophenyl)-1,4-dihydro-2,6-dimethylpyridine-3,5-dicarboxylate

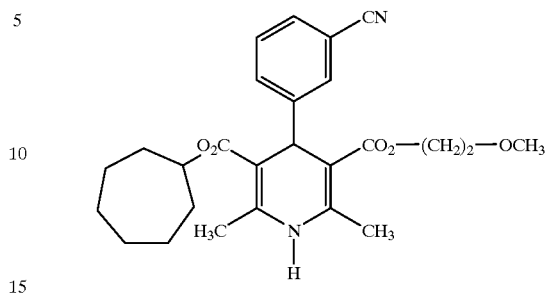

5.0 g (14 mmol) of (–)-4-(3-cyanophenyl)-1,4-dihydro-2,6-dimethyl-3-(2-methoxy)ethoxycarbonylpyridine-5-carboxylic acid [obtainable by chromatographic separation of the racemic monocarboxylic acid on chiral stationary phases] are stirred over molecular sieve (4 A) for 30 min in 50 ml of tetrahydrofuran. 2.3 g (14 mmol) of carbonyldiimidazole are then added and the mixture is heated to reflux for 1 h, the molecular sieve is filtered off and the filtrate is concentrated. The residue is taken up in 30 ml of cycloheptanol and heated at 100° C. for 6 h after addition of a spatula-tipful of N,N-dimethyl-4-aminopyridine. Repeated chromatography on silica gel in toluene/ethyl acetate, dichloromethane/isopropanol and cyclohexane/ethyl acetate mixtures and crystallization from diisopropyl ether/cyclohexane yields 1.0 g (16%) of the target compound as white crystals.

M.p.: 98–99° C.
$[\alpha]_D^{30}$=–24.2° (c=0.9, CHCl$_3$)

The compounds shown in Table 1 are obtained in analogy to Examples 1 and 2, or by subjecting the racemic products to chromatographic separation into the enantiomerically pure target compounds on chiral stationary phases (Chiralcel and Chiralpak, Daicel):

TABLE 1

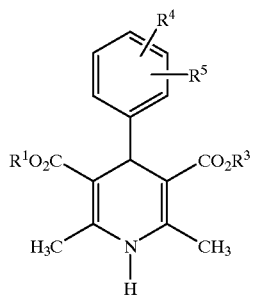

| Ex. No. | R$^1$ | R$^4$ | R$^5$ | R$^3$ | Racemate/enantiomer | M.p. (° C.) | $[\alpha]_D^{20}$ |
|---|---|---|---|---|---|---|---|
| 3 | H$_3$C—O—(CH$_2$)$_2$— | 2-Cl | 6-F | —CH(CH$_3$)$_2$ | racemate | 57–59 | |
| 4 | H$_3$C—O—(CH$_2$)$_2$— | 2-Cl | 6-F | —CH(CH$_3$)$_2$ | (+)-enantiomer | | |
| 5 | H$_3$C—O—(CH$_2$)$_2$— | 2-Cl | 6-F | —CH(CH$_3$)$_2$ | (–)-enantiomer | | |
| 6 | H$_3$C—O—(CH$_2$)$_2$ | 2-F | 6-F | —CH(CH$_3$)$_2$ | racemate | 119–120 | |
| 7 | H$_3$C—O—(CH$_2$)$_2$ | 2-F | 6-F | —CH(CH$_3$)$_2$ | (+)-enantiomer | | +17.8(c = 0.5; CH$_2$Cl$_2$) |
| 8 | H$_3$C—O—(CH$_2$)$_2$ | 2-F | 6-F | —CH(CH$_3$)$_2$ | (–)-enantiomer | | –27(c = 0.73; CH$_2$Cl$_2$) |
| 9 | H$_3$C—O—(CH$_2$)$_2$ | 2-F | 3-F | —CH(CH$_3$)$_2$ | racemate | 135–136 | |
| 10 | H$_3$C—O—(CH$_2$)$_2$ | 2-F | 3-F | —CH(CH$_3$)$_2$ | (+)-enantiomer | | |
| 11 | H$_3$C—O—(CH$_2$)$_2$ | 2-F | 3-F | —CH(CH$_3$)$_2$ | (–)-enantiomer | | |
| 12 | H$_3$C—O—(CH$_2$)$_2$ | 2-Cl | 5-Cl | —CH(CH$_3$)$_2$ | racemate | 79–89 | |
| 13 | H$_3$C—O—(CH$_2$)$_2$ | 2-Cl | 5-Cl | —CH(CH$_3$)$_2$ | (+)-enantiomer | | +24.6(c = 1.51; CHCl$_3$) |
| 14 | H$_3$C—O—(CH$_2$)$_2$ | 2-Cl | 5-Cl | —CH(CH$_3$)$_2$ | (–)-enantiomer | | –24.9(c = 1.44; CHCl$_3$) |

TABLE 1-continued

[Structure: 1,4-dihydropyridine with 2,6-dimethyl, 3-CO2R3, 5-CO2R1, and 4-aryl (with R4, R5 substituents)]

| Ex. No. | R¹ | R⁴ | R⁵ | R³ | Racemate/enantiomer | M.p. (° C.) | $[\alpha]_D^{20}$ |
|---|---|---|---|---|---|---|---|
| 15 | —CH(CH₃)₂ | 2-CN | 3-Cl | —(CH₂)₂—OCH₃ | racemate | 151–152 | |
| 16 | —CH(CH₃)₂ | 2-CN | 3-Cl | —(CH₂)₂—OCH₃ | (+)-enantiomer | 149–151 | +10.9(c = 1.0; CHCl₃) |
| 17 | —CH(CH₃)₂ | 2-CN | 3-Cl | —(CH₂)₂—OCH₃ | (−)-enantiomer | 149–150 | −12.7(c = 1.0; CHCl₃) |
| 18 | H₃C—O—(CH₂)₂— | 3-F | 4-F | —CH(CH₃)₂ | racemate | 78 | |
| 19 | H₃C—O—(CH₂)₂— | 3-F | 4-F | —CH(CH₃)₂ | (+)-enantiomer | | |
| 20 | H₃C—O—(CH₂)₂— | 3-F | 4-F | —CH(CH₃)₂ | (−)-enantiomer | | |
| 21 | H₃C—O—(CH₂)₂— | 2-F | 5-F | —CH(CH₃)₂ | racemate | 104–106 | |
| 22 | H₃C—O—(CH₂)₂— | 2-F | 5-F | —CH(CH₃)₂ | (+)-enantiomer | 113 | |
| 23 | H₃C—O—(CH₂)₂— | 2-F | 5-F | —CH(CH₃)₂ | (−)-enantiomer | 113 | −22.8(c = 0.96; CHCl₃) |
| 24 | —CH(CH₃)₂ | 2-CN | H | —(CH₂)₂—OCH₃ | racemate | 123–125 | |
| 25 | —CH(CH₃)₂ | 2-CN | H | —(CH₂)₂—OCH₃ | (+)-enantiomer | 124–125 | +5.5(c = 0.9; CHCl₃) |
| 26 | —CH(CH₃)₂ | 2-CN | H | —(CH₂)₂—OCH₃ | (−)-enantiomer | 122–123 | −8.2(c = 1.0; CHCl₃) |
| 27 | H₃C—O—(CH₂)₂— | 2-F | 3-CF₃ | —CH(CH₃)₂ | racemate | 140–142 | |
| 28 | H₃C—O—(CH₂)₂— | 2-F | 3-CF₃ | —CH(CH₃)₂ | (+)-enantiomer | | |
| 29 | H₃C—O—(CH₂)₂— | 2-F | 3-CF₃ | —CH(CH₃)₂ | (−)-enantiomer | | |
| 30 | H₃C—O—(CH₂)₂— | 2-Cl | 3-CN | methylcyclopentyl | racemate | 119–120 | |
| 31 | H₃C—O—(CH₂)₂— | 2-Cl | 3-CN | methylcyclopentyl | (+)-enantiomer | | |
| 32 | H₃C—O—(CH₂)₂— | 2-Cl | 3-CN | methylcyclopentyl | (−)-enantiomer | | |
| 33 | —C(CH₃)₃ | H | 3-CN | —(CH₂)₂—OCH₃ | racemate | 108–109 | |
| 34 | —C(CH₃)₃ | H | 3-CN | —(CH₂)₂—OCH₃ | (+)-enantiomer | | |
| 35 | —C(CH₃)₃ | H | 3-CN | —(CH₂)₂—OCH₃ | (−)-enantiomer | | |
| 36 | H₃C—O—(CH₂)₂— | 2-F | 3-CF₃ | methylcyclopentyl | racemate | 105 | |

TABLE 1-continued

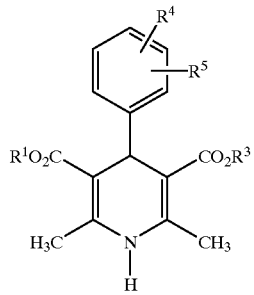

| Ex. No. | R¹ | R⁴ | R⁵ | R³ | Racemate/enantiomer | M.p. (° C.) | $[\alpha]_D^{20}$ |
|---|---|---|---|---|---|---|---|
| 37 | H₃C—O—(CH₂)₂— | 2-F | 3-CF₃ | 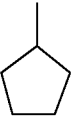 | (+)-enantiomer | | |
| 38 | H₃C—O—(CH₂)₂— | 2-F | 3-CF₃ | 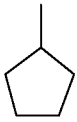 | (−)-enantiomer | | |
| 39 | H₃C—O—(CH₂)₂— | 2-F | 3-CF₃ | —CH₃ | racemate | 128 | |
| 40 | H₃C—O—(CH₂)₂— | 2-F | 3-CF₃ | —CH₃ | (+)-enantiomer | | |
| 41 | H₃C—O—(CH₂)₂— | 2-F | 3-CF₃ | —CH₃ | (−)-enantiomer | | |
| 42 | 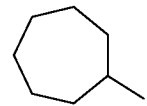 | H | 3-CN | —(CH₂)₂—OCH₃ | racemate | 138–140 | |
| 43 | 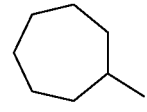 | H | 3-CN | —(CH₂)₂—OCH₃ | (+)-enantiomer | 98–99 | +21.8(c = 0.96; CHCl₃) |
| 44 | —CH(CH₃)₂ | 2-F | H | —(CH₂)₂—OCH₃ | (+)-enantiomer | oil | +21.9(c = 0.96; CHCl₃) |
| 45 | —CH(CH₃)₂ | 2-F | H | —(CH₂)₂—OCH₃ | (−)-enantiomer | oil | −23.5(c = 0.96; CHCl₃) |
| 46 | 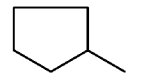 | 2-CN | 3-Cl | —(CH₂)₂—OCH₃ | racemate | 128–130 | |
| 47 | 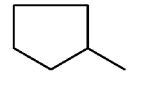 | 2-CN | 3-Cl | —(CH₂)₂—OCH₃ | (+)-enantiomer | | |
| 48 | 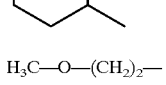 | 2-CN | 3-Cl | —(CH₂)₂—OCH₃ | (−)-enantiomer | | |
| 49 | H₃C—O—(CH₂)₂— | 2-Cl | 5-CN | —CH(CH₃)₂ | racemate | 155–157 | |
| 50 | 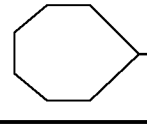 | H | 3-CN | —(CH₂)₂—OCH₃ | (−)-enantiomer | 98–99 | −24.2(c = 0.9, CHCl₃) |

Example 51

2-Methoxyethyl Isopropyl 5-(2,4-difluorophenyl)-1,4-dihydro-2,6-dimethylpyridine-3,5-dicarboxylate

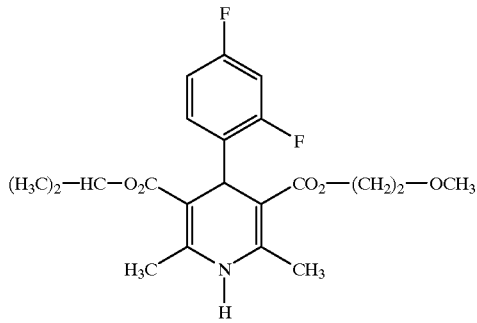

5.0 g (about 18 mmol) of the compound from Example IV are heated to reflux overnight in 50 ml of isopropanol with 2.5 g (18 mmol) of isopropyl 3-amino-2-butenoate. After thin-layer chromatographic checking (SiO$_2$, toluene/ethyl acetate 5:1) shows complete conversion, the reaction mixture is concentrated, the residue is taken up with toluene, the solution is concentrated again and the residue is then purified by crystallization from a little methanol. 2.8 g (39%) of the target compound are obtained.

M.p.: 123–126° C.

The compounds shown in Tables 2, 3, 4, 5, 6 and 7 are prepared in analogy to the procedure of Examples 1, 2 and 51:

TABLE 2

| Ex. No. | R$^4$ | R$^5$ | M.p. [° C.] |
|---|---|---|---|
| 52 | 3-F | H | 90–93 |
| 53 | 2-Cl | 4-Cl | 116–118 |
| 54 | 3-Cl | 4-Cl | 55–60 |
| 55 | 3-Cl | 5-Cl | 100–102 |
| 56 | 2-Cl | 6-Cl | 100 |
| 57 | 2-F | 5-Cl | 100–101 |
| 58 | 3-Cl | 4-Cl | 79–81 |
| 59 | 2-CH$_3$ | 3-F | 136 |
| 60 | 2-C≡CH | 3-Cl | 146 |
| 61 | 2-Cl | 5-C≡CH | 100–103 |
| 62 | 2-C≡CH | 4-F | 82–85 |
| 63 | 3-OCF$_3$ | H | 45 |
| 64 | 2-SCH$_3$ | 5-Br | 97–98 |
| 65 | 2-OCH$_3$ | 3-F | 136 |
| 66 | 2-OCH$_3$ | 6-F | 112 |
| 67 | 2-OCH$_3$ | 5-F | 104 |
| 68 | 2-F | 5-OCH$_3$ | 0.35$^{a)}$ |
| 69 | 3-Cl | H | 143 |
| 70 | 2-OCH$_3$ | 6-Cl | 135 |
| 71 | 2-Cl | 5-CN | 155–157 |
| 72 | 2-OCH$_3$ | 5-Cl | 143 |
| 73 | 2-F | 5-F | oil |

$^{a)}$ = cyclohexane:ethyl acetate 1:1

TABLE 3

| Ex. No. | R$^1$ | M.p. [° C.]/R$_f$* |
|---|---|---|
| 74 | isobutyl | 0.15$^{b)}$ |
| 75 | 2-methylbutyl | 90 |
| 76 | cyclopentylmethyl | 104 |
| 77 | cyclohexylmethyl | 88 |

$^{b)}$toluene:ethyl acetate 10:1

TABLE 4
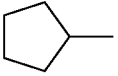
| Ex. No. | R¹ | R³ | M.p. [° C.]/R$_f$* |
|---|---|---|---|
| 78 | —CH(CH$_3$)$_2$ | n-(CH$_2$)$_3$CH$_3$ | 112 |
| 79 | cyclopentyl-CH$_2$— | n-(CH$_2$)$_3$CH$_3$ | 109 |
TABLE 5
| Ex. No. | R¹ | R³ | M.p. [° C.]/R$_f$* |
|---|---|---|---|
| 80 | —CH$_3$ | —(CH$_2$)$_3$OCH$_3$ | 131 |
| 81 | —CH(CH$_3$)$_2$ | —(CH$_2$)$_3$OH | 138 |
| 82 | —CH(CH$_3$)$_2$ | —(CH$_2$)$_3$OC$_2$H$_5$ | 103 |
| 83 | —CH(CH$_3$)$_2$ | —(CH$_2$)$_3$OCH(CH$_3$)$_2$ | 99 |
| 84 | —CH(CH$_3$)$_2$ | —(CH$_2$)$_3$O—CH$_2$—CH(CH$_3$)$_2$ | 67–70 |
| 85 | —CH(CH$_3$)$_2$ | —(CH$_2$)$_3$O—C(CH$_3$)$_3$ | 103–104 |
| 86 | —CH(CH$_3$)$_2$ | —(CH$_2$)$_4$OCH$_3$ | 0.24[c)] |
| 87 | —CH(CH$_3$)$_2$ | —CH$_2$C(CH$_3$)(C$_2$H$_5$)CH$_2$OCH$_3$ | 0.16[c)] |

TABLE 5-continued
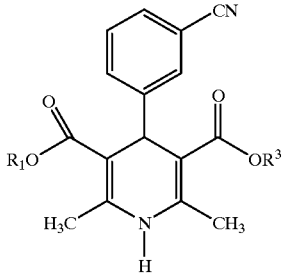
| Ex. No. | R¹ | R³ | M.p. [° C.]/$R_f$* |
|---|---|---|---|
| 88 | —CH₂—CH(CH₃)₂ | 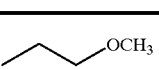 | 136 |
| 89 | 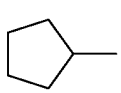 | 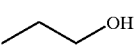 | 152–153 |
| 90 | 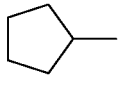 | 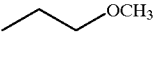 | 162–163 |
| 91 | 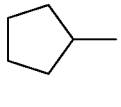 |  | 127–128 |
| 92 | 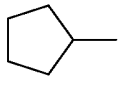 |  | 106–107 |
| 93 | 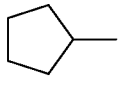 | 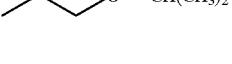 | 99 |
| 94 | 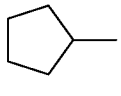 | 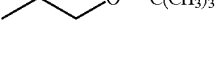 | 122–123 |
| 95 | 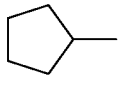 | 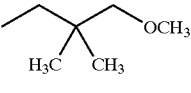 | 0.56[d] |
| 96 | 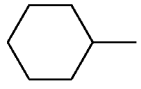 | 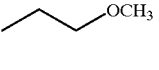 | 125–127 |
| 97 | 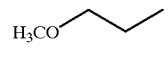 | 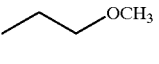 | 126 |
[c] = toluene:ethyl acetate 3:1
[d] = toluene:ethyl acetate 1:1

TABLE 6

| Ex. No. | R¹ | R⁴ | R⁵ | R³ | M.p. (° C.) | Preparation analogously to Example No. |
|---|---|---|---|---|---|---|
| 98 | H₃CO–CH₂CH₂– | 2-Cl | 5-CN | cyclopentyl | 176–177 | |
| 99 | CH₃ | 2-CN | 3-Cl | cyclopentyl | 221–222 | |
| 100 | —C(CH₃)₃ | 2-F | 6-F | —(CH₂)₂OCH₃ | 0.23$^{d)}$ | |
| 101 | cyclopentyl | 2-F | 3-F | —(CH₂)₂—O—CH(CH₃)₂ | 85–86.5 | |
| 102 | cyclopentyl | 2-F | 3-F | —(CH₂)₂OH | 141–142 | |
| 103 | —CH(CH₃)₂ | 2-F | 3-F | —(CH₂)₂—OH | 139 | 2 |
| 104 | —CH(CH₃)₂ | 2-F | 3-F | —(CH₂)₂—O—CH(CH₃)₂ | 96 | 2 |
| 105 | cycloheptyl | 2-F | 5-F | —(CH₂)₂OCH₃ | 0.17$^{e)}$ | 2 |

TABLE 7

| Ex. No. | R¹ | R⁴ | R⁵ | R³ | Yield (% of theory) | R$_f$* | Preparation analogously to Example No. |
|---|---|---|---|---|---|---|---|
| 106 | —CH(CH₃)₂ | 2-F | 5-F | —H₂C—C(CH₃)₂—OH | 77 | 0.3$^{d)}$ | 2 |

$^{d)}$toluene/ethyl acetate 1:1
*Use of 1.1 mol equivalent each of alcohol (R³OH) and NaH suspension (relative to imidazolide) in THF

Example 107

Methyl 2-methoxyethyl (−)-4-(3-cyanophenyl)-1,4-dihydro-2,6-dimethylpyridine-3,5-dicarboxylate

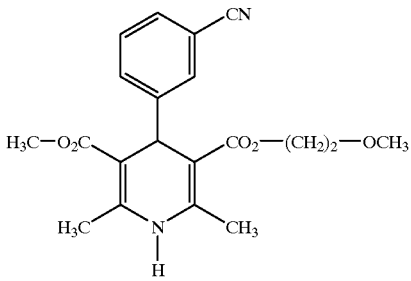

3.6 g (10 mmol) of (−)-4-(3-cyanophenyl)-1,4-dihydro-3-(2-methoxy)ethoxycarbonyl-2,6-dimethylpyridine-5-carboxylic acid are stirred over molecular sieve (4 A) for 30 min in 40 ml of tetrahydrofuran. 1.6 g (10 mmol) of carbonyldiimidazole are then added and the mixture is heated at 60° C. for 0.5 h, the molecular sieve is filtered off and the filtrate is concentrated. The residue is taken up in 40 ml of methanol and heated at 80° C. for 6 h. Repeated chromatography on silica gel using toluene/ethyl acetate mixtures (1:0 to 3:1) yields 1.4 g of oily substance which are crystallized by triturating with diethyl ether. 1.1 g (30%) of colourless crystals of m.p. 103–104° C. are thus obtained.

$[\alpha]_D^{20} = -7.0°$ (c=1.2; CHCl$_3$)

The compounds shown in Table 8 are obtained in analogy to Example 107 or by subjecting the racemic products to chromatographic separation into the enantiomerically pure target compounds (A* in the following) on chiral stationary phases (Chiralcel and Chiralpak, Daicel):

TABLE 8

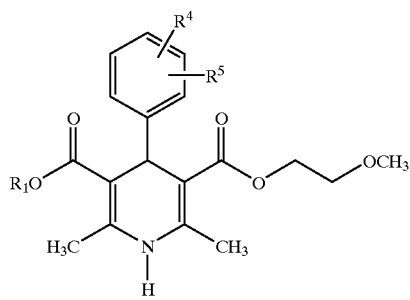

| Ex. No. | R$^1$ | R$^4$ | R$^5$ | Enantiomer | M.p. (° C.) | $[\alpha]_D^{20}$ | Preparation analogously to Process/Example No. |
|---|---|---|---|---|---|---|---|
| 108 | —CH$_3$ | H | 3-CN | (+) | 103–104 | +5.4(c = 1.0, CHCl$_3$) | 107 |
| 109 | —CH(CH$_3$)$_2$ | H | 3-CN | (+) | 127–128 | +14(c = 1.0, CHCl$_3$) | 107 |
| 110 | —CH(CH$_3$)$_2$ | H | 3-CN | (−) | 127–128 | −13.3(c = 1.2, CHCl$_3$) | 107 |
| 111 | —CH(CH$_3$)$_2$ | 2-Cl | 5-CN | (+) |  | +33(c = 1.0, CH$_3$OH) | A* |
| 112 | —CH(CH$_3$)$_2$ | 2-Cl | 5-CN | (−) |  | −30(c = 0.3; CH$_3$OH) | A* |

Example 113

Bis-(2-methoxyethyl) 4-(2-fluoro-3-trifluoromethylphenyl)-1,4-dihydro-2,6-dimethylpyridine-3,5-dicarboxylate

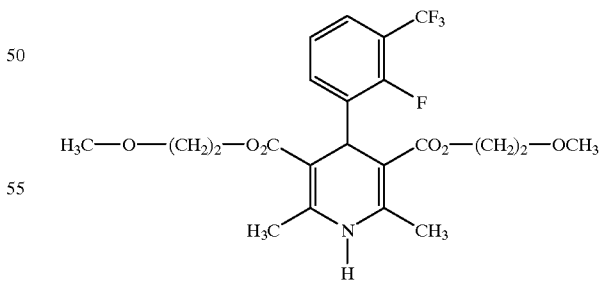

5 ml of a 25% strength ammonia solution and 5.0 g (31.2 mmol) of 2-methoxyethyl acetoacetate are added to a solution of 3.0 g (15.6 mmol) of 2-fluoro-3-trifluoromethylbenzaldehyde in 50 ml of dioxane and the mixture is heated to reflux until TLC checking (silica gel, toluene/ethyl acetate 5:1) indicates complete conversion. The mixture is concentrated, the residue is taken up twice in toluene and the solution is concentrated again. Crystallization from toluene yields 1.4 g (19%) of the target compound of melting point 148° C.

The examples shown in Table 9 are prepared in analogy to the procedure of Example 113:

TABLE 9

| Ex. No. | R¹ and R³ | R⁴ | R⁵ | M.p. (° C.)/$R_f$ |
|---|---|---|---|---|
| 114 | —(CH₂)₂—OCH₃ | 2-Cl | 5-Cl | 78 |
| 115 | —(CH₂)₂—OCH₃ | 2-F | 5-F | 130 |
| 116 | —(CH₂)₃—OCH₃ | 2-Cl | 5-Cl | 76 |
| 117 | —(CH₂)₃—OCH₃ | 2-F | 5-F | 97 |

TABLE 9-continued

| Ex. No. | R¹ and R³ | R⁴ | R⁵ | M.p. (° C.)/$R_f$ |
|---|---|---|---|---|
| 118 | (neopentyl-OCH₃ group) | 2-Cl | 5-Cl | 0.29(cyclohexane/ethyl acetate 2:1) |
| 119 | (neopentyl-OCH₃ group) | 2-F | 5-F | 106 |

The compounds shown in Table 10 are prepared from the corresponding imidazolide in analogy to the procedure of Example 107:

TABLE 10

| Ex. No. | R¹ | R⁴ | R⁵ | R³ | M.p. (° C.)/$R_f$* |
|---|---|---|---|---|---|
| 120 | —CH₃ | 2-F | 3-F | —(CH₂)₂—OCH₃ | 123 |
| 121 | H₃CO—(CH₂)₂ | 2-F | 3-F | —(CH₂)₂—OCH₃ | 141–142 |
| 122 | H₃CO—(CH₂)₂— | 2-Cl | H | —(CH₂)₂—OCH₃ | 126–127 |
| 123 | —CH(CH₃)₂ | 2-Cl | H | —(CH₂)₂—OCH₃ | 105 |
| 124 | —CH(CH₃)₂ | 2-Cl | H | —CH₂—C(CH₃)₂—CH₂OH | 128–129 |

What is claimed is:

1. A compound of the formula

wherein $R^1$, $R^4$, $R^5$ and $R^3$ are selected from

| $R^1$ | $R^4$ | $R^5$ | $R^3$ | racemate/enantiomer (rac/+, −) |
|---|---|---|---|---|
| cycloheptyl | H | 3-CN | —CH$_2$—(CH$_2$)$_2$—OCH$_3$ | (−) |
| —CH(CH$_3$)$_2$ | 2-CN | 3-Cl | —(CH$_2$)$_2$—OCH$_3$ | rac |
| —CH(CH$_3$)$_2$ | 2-CN | 3-Cl | —(CH$_2$)$_2$—OCH$_3$ | (+) |
| —CH(CH$_3$)$_2$ | 2-CN | 3-Cl | —(CH$_2$)$_2$—OCH$_3$ | (−) |
| H$_3$C—O—(CH$_2$)$_2$— | 2-Cl | 3-CN | methylcyclopentyl | rac |
| H$_3$C—O—(CH$_2$)$_2$— | 2-Cl | 3-CN | methylcyclopentyl | (+) |
| H$_3$C—O—(CH$_2$)$_2$— | 2-Cl | 3-CN | methylcyclopentyl | (−) |
| cycloheptylmethyl | H | 3-CN | —(CH$_2$)$_2$—OCH$_3$ | rac |
| cycloheptylmethyl | H | 3-CN | —(CH$_2$)$_2$—OCH$_3$ | (+) |
| cyclopentylmethyl | 2-CN | 3-Cl | —(CH$_2$)$_2$—OCH$_3$ | rac |
| cyclopentylmethyl | 2-CN | 3-Cl | —(CH$_2$)$_2$—OCH$_3$ | (+) |
| cyclopentylmethyl | 2-CN | 3-Cl | —(CH$_2$)$_2$—OCH$_3$ | (−) |
| H$_3$C—O—(CH$_2$)$_2$— | 2-Cl | 5-CN | —CH(CH$_3$)$_2$ | rac |
| cycloheptylmethyl | H | 3-CN | —(CH$_2$)$_2$—OCH$_3$ | (−) |
| (CH$_3$)$_2$HC | 2-Cl | 5-CN | —(CH$_2$)$_2$—OCH$_3$ | rac |
| —CH(CH$_3$)$_2$ | 3-CN | H | —(CH$_2$)$_3$—OC$_2$H$_5$ | rac |
| —CH(CH$_3$)$_2$ | 3-CN | H | —(CH$_2$)$_3$—OCH(CH$_3$)$_2$ | rac |
| —CH(CH$_3$)$_2$ | 3-CN | H | —(CH$_2$)$_2$—O—CH$_2$—CH(CH$_3$)$_2$ | rac |
| —CH(CH$_3$)$_2$ | 3-CN | H | —(CH$_2$)$_3$—O—C(CH$_3$)$_3$ | rac |
| —CH(CH$_3$)$_2$ | 3-CN | H | —(CH$_2$)$_3$—OCH$_3$ | rac |
| —CH(CH$_3$)$_2$ | 3-CN | H | —CH$_2$—C(CH$_3$)(C$_2$H$_5$)—OCH$_3$ | rac |
| CH$_2$—CH(CH$_3$)$_2$ | 3-CN | H | —(CH$_2$)$_3$—OCH$_3$ | rac |
| cyclopentylmethyl | 3-CN | H | —(CH$_2$)$_3$—OCH$_3$ | rac |
| cyclopentylmethyl | 3-CN | H | —(CH$_2$)$_3$—OC$_2$H$_6$ | rac |
| cyclopentylmethyl | 3-CN | H | —(CH$_2$)$_3$—O—CH(CH$_3$)$_2$ | rac |
| cyclopentylmethyl | 3-CN | H | —(CH$_2$)$_3$—O—CH(CH$_3$)$_2$ | rac |
| cyclopentylmethyl | 3-CN | H | —(CH$_2$)$_3$—O—C(CH$_3$)$_3$ | rac |
| cyclopentylmethyl | 3-CN | H | —CH$_2$—C(CH$_3$)(C$_2$H$_5$)—OCH$_3$ | rac |
| cyclohexylmethyl | 3-CN | H | —(CH$_2$)$_3$—OCH$_3$ | rac |
| H$_3$CO—(CH$_2$)$_3$— | 2-Cl | 5-CN | methylcyclopentyl | rac |
| —CH(CH$_3$)$_2$ | 2-Cl | 5-CN | —(CH$_2$)$_2$—OCH$_3$ | (+) |
| —CH(CH$_3$)$_2$ | 2-Cl | 5-CN | —(CH$_2$)$_2$—OCH$_3$ | (−). |

2. A compound selected from the group consisting of

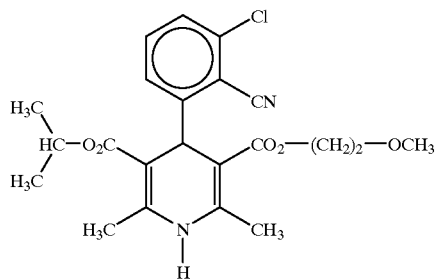

and

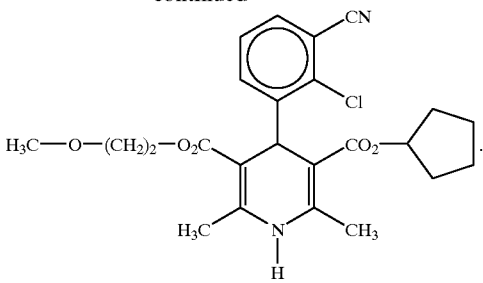

3. A pharmaceutical composition which comprises an effective amount of a compound according to claim 1 and a pharmaceutically acceptable carrier or excipient.

4. A pharmaceutical composition which comprises an effective amount of a compound according to claim 2 and a pharmaceutically acceptable carrier or excipient.

* * * * *